(12) United States Patent
Tanaka et al.

(10) Patent No.: US 6,480,732 B1
(45) Date of Patent: Nov. 12, 2002

(54) MEDICAL IMAGE PROCESSING DEVICE FOR PRODUCING A COMPOSITE IMAGE OF THE THREE-DIMENSIONAL IMAGES

(75) Inventors: Yuko Tanaka, Shioya-gun; Hitoshi Yamagata, Otawara, both of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 82 days.

(21) Appl. No.: 09/609,032

(22) Filed: Jun. 30, 2000

(30) Foreign Application Priority Data

Jul. 1, 1999 (JP) ............................................ 11-187969

(51) Int. Cl.$^7$ ................................................. A61B 5/05
(52) U.S. Cl. ........................ 600/425; 600/411; 600/427; 600/441; 382/128; 128/922
(58) Field of Search ................................ 600/411, 425, 600/427, 441; 128/922; 382/128

(56) References Cited

U.S. PATENT DOCUMENTS

| | | | | |
|---|---|---|---|---|
| 6,151,009 A | * | 11/2000 | Kanade et al. | 345/641 |
| 6,167,296 A | * | 12/2000 | Shahidi | 600/117 |
| 6,283,918 B1 | * | 9/2001 | Kanda et al. | 128/916 |

* cited by examiner

*Primary Examiner*—Marvin M. Lateef
*Assistant Examiner*—Runa Shoh Qaderi
(74) *Attorney, Agent, or Firm*—Oblon, Spivak, McClelland, Maier & Neustadt, P.C.

(57) ABSTRACT

First and second volume data are collected in advance for the same region of a human body under examination. By performing volume rendering along the set direction of line of sight, a composite image of a first three-dimensional image based on the first volume data and a second three-dimensional image based on the second volume data is produced. The volume rendering is performed taking into consideration whether the trimming of the front region has been specified or not. In the volume rendering, by setting the initial position of a point of interest on the plane of projection or on the plane section indicated by a depth map according to whether the trimming of the front region has been specified or not, a three-dimension imaging region is varied. When the trimming of the front region has been specified, the initial position of the point of interest is set on the plane of projection. Otherwise, the depth map is examined for value $D1(x,y)$ of the point of interest and, if the value is less than the maximum depth Dmax, the initial position of the point of interest is set on the plane section. That is, the depth is set to $D1(x, y)$. If the value is greater than maximum depth Dmax, the initial position of the point of interest is set on the plane of projection. That is, the depth is initialized to 0.

9 Claims, 5 Drawing Sheets

MEDICAL IMAGE PROCESSING DEVICE FOR PRODUCING A COMPOSITE IMAGE OF THE THREE-DIMENSIONAL IMAGES

CROSS-REFERENCE TO RELATED APPLICATIONS

This application is based upon and claims the benefit of priority from the prior Japanese Patent Application No. 11-187969, filed Jul. 1, 1999, the entire contents of which are incorporated herein by reference.

BACKGROUND OF THE INVENTION

The present invention relates to a medical image processing device used in combination with various types of imaging diagnostic apparatuses, such as an ultrasonic diagnostic (imaging) apparatus, an X-ray computerized tomography (CT) apparatus, a magnetic resonance imaging (MRI) apparatus, a nuclear medical diagnostic apparatus and so on. More specifically, the present invention relates to an image processing device which is adapted to produce a composite image by subjecting two or more pieces of volume data obtained for the same region of a human body under examination through different imaging techniques to three-dimensional image processing.

The X-ray computerized tomography apparatus, one of medical imaging diagnostic apparatuses, is adapted to image the distribution of transmissions of X-rays through a human body under examination. The nuclear medical diagnostic apparatus is adapted to image the distribution of gamma rays emitted from a radioactive isotope taken by a human subject. The physical quantities of a human body for imaging vary according to types of medical imaging diagnostic apparatuses. Even one imaging diagnostic apparatus can image different physical quantities by switching its imaging modes. For example, the ultrasonic diagnostic apparatus generally has at least two imaging modes built in: B mode and Doppler mode. In the B mode, variations in transmission velocity of ultrasound within a human body are imaged as variations in brightness. In the Doppler mode, the velocity of a moving object, such as blood, and its flow rate are imaged.

In order to improve diagnosis accuracy, it is desired that doctors be able to observe some types of medical images having different physical characteristics and clinical values in combination. Heretofore, not only a single image has been displayed, but also images obtained by different types of imaging diagnostic apparatuses or images obtained in different imaging modes have been displayed side by side.

To be specific, in ultrasonic imaging diagnosis of, for example, a liver tumor, a B-mode image is used to identify the size, position and internal structure of the tumor and, at the same time, the positions of blood vessels running around the tumor are identified using a Doppler image. Thereby, the position relationship of the tumor and the blood vessels is identified. In addition, a blood vessel, which extends from a vegetative blood vessel giving nutrition to the tumor, is identified to determine the size of the vegetative blood vessels with respect to the tumor. Based on these results, the tumor is diagnosed with respect to the position, the degree of malignancy and the degree of progress.

Within the liver, arteries, veins and portal veins run three-dimensionally and intricately. In order to understand the relationship between the three-dimensionally running blood vessels and the tumor, doctors are required to have a high level of knowledge and experience. In giving medical treatment on the basis of the results of diagnosis, a doctor who made diagnosis must accurately present the relationship between the blood vessels and the tumor to a doctor in charge of treatment. In this case as well, a high level of knowledge and experience is required.

Thus, in ultrasonic imaging diagnosis of a liver tumor, a B-mode image and a Doppler image have been displayed in combination in order to allow doctors to readily understand the relationship between blood vessels running in three dimensions and the tumor.

At actual medical sites, an approach has been taken by which a two-dimensional Doppler image is displayed combined with a two-dimensional B-mode image. To further improve the diagnostic ability, an approach has been proposed by which a three-dimensional B-mode image and a three-dimensional Doppler image are respectively reconstructed from two-dimensional B-mode images and two-dimensional Doppler images which have been collected in a spatially continuous form and then displayed in combination.

Methods of producing three-dimensional medical images include surface rendering for displaying the surface extracted by means of thresholding from volume data in three dimensions, volume rendering for allocating an opacity or color to each of pixel values that make up volume data and displaying the data itself, and MPR which cuts out an arbitrary plane section from volume data and displays an image of that plane section.

According to the surface rendering, by extracting the surface of the tumor or blood vessels, their three-dimensional surface configuration, location and running state can be displayed. Likewise, in the volume rendering, by allocating a high level of opacity to each of pixels in regions corresponding to the tumor or blood vessels, their three-dimensional surface configuration, location and running state can be displayed.

However, according to surface rendering-based and volume rendering-based images, the three-dimensional configuration and the position of a target can be observed, but it is difficult to observe the internal structure of a tumor and blood vessels running within the tumor. On the other hand, with MPR-based images, the internal structure of a tumor can be observed by setting up a plane section in the tumor, but it is difficult to observe the three-dimensional configurations and positions of a tumor and blood vessels and the running states of the blood vessels within the tumor.

In three-dimensionally combining images of a liver tumor and images of blood vessels, a mere combination of surface rendering versions of B-mode and Doppler images, volume rendering versions of B-mode and Doppler images, or MPR versions of B-mode and Doppler images causes a problem that it is hard to understand the position relationship of the tumor and the blood vessels.

For this reason, a three-dimensional image display technique has been demanded which combines MPR versions of B-mode images and surface rendering or volume rendering versions of Doppler images and displays both the three-dimensional running state of blood vessels and the internal structure of a tumor simultaneously in an easily understandable manner.

In three-dimensional imaging, it may be supposed that a part of an MPR image of a plane section of a tumor is veiled from a point of view with a three-dimensional image of blood vessels. In such an event, it will become difficult to tell whether the displayed blood vessels pass through the cutout plane section of the tumor or run outside the plane section. This constitutes an obstruction to imaging diagnosis, failing to provide information useful in giving medical treatment.

BRIEF SUMMARY OF THE INVENTION

It is therefore an object of the present invention to provide a three-dimensional medical image composite display device which produces an image useful in imaging diagnosis and treatment by performing three-dimensional image composition processing on two or more types of volume data obtained for the same region of a human body under examination through different imaging techniques.

According to the present invention, there is provided a medical image processing device for producing a plurality of three-dimensional images for the same region of a human body under examination and combining the three-dimensional images to produce a composite image for display, comprising:

input means for setting a plane section of the region of the human body under examination;

first image projection means, responsive to first three-dimensional data for the same region of the human body under examination, for producing a three-dimensional image containing the plane section set by the input means;

input means for specifying the display/non-display of a region of the human body under examination;

second image producing means, responsive to second three-dimensional image data for the same portion of the human body under examination, for producing a three-dimensional image having data on one side of the plane section removed; and combining means for combining the three-dimensional image containing the plane section produced by the first image producing means and the three-dimensional image produced by the second image production means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
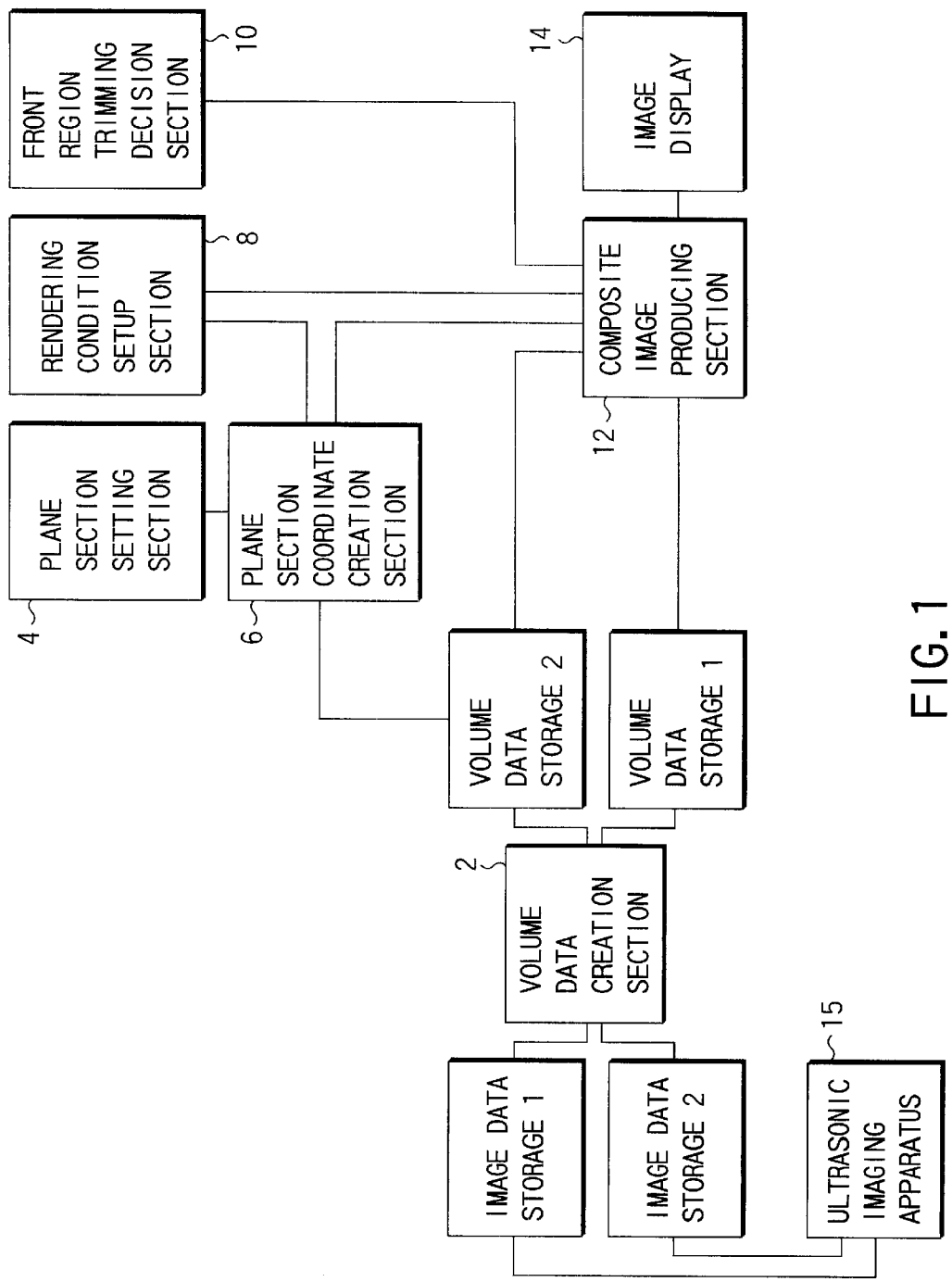
FIG. 1 is a schematic block diagram of a three-dimensional medical image composite display device according to an embodiment of a medical image processing device of the present invention.

Referring now to FIG. 1, there is illustrated, in block diagram form, a three-dimensional medical image composite display device according to an embodiment of a medical image processing device of the present invention. The device comprises image data storage sections 1 and 2, a volume data creation section 2, volume data storage sections 1 and 2, a plane position setting section 4, a plane coordinate creation section 6, a rendering condition setup section 8, a front-region trimming decision section 10, a composite image producing section 12, and an image display unit 14. This device is attached to an ultrasonic imaging apparatus as a medical image collecting apparatus. As will be described later in connection with the description of other embodiments, the medical image processing device of the present invention may be attached to a magnetic resonance imaging (MRI) apparatus, an X-ray computerized tomography (CT) apparatus, a nuclear medical diagnostic apparatus (gamma camera), or the like.

The image data storage section 1 is supplied with image data of first images and position information of these images from the ultrasonic imaging apparatus 15. Here, the first images are defined to be multiple B-mode images that are collected through three-dimensional scanning of ultrasound by the ultrasonic imaging apparatus 15 and each differ in the position of plane section. A B-mode image is a cross-sectional image of organ tissues of a human body under examination.

The image data storage section 2 is supplied with image data of second images and position information of these images from the ultrasonic imaging apparatus 15. Here, the second images are defined to be multiple Doppler images that are collected through three-dimensional scanning of ultrasound by the ultrasonic imaging apparatus 15 at the same instants of time as above and each differ in the position of plane section. A Doppler image is an image of moving objects (e.g., blood flow) of the same human body under examination.

The volume data creation section 2 reads image data of each of the first images and corresponding position information from the image data storage section 1. Each pixel data in the read image data is placed in a corresponding position on a three-dimensional storage region on the basis of the read position information. This process is repeated for all of the first images. In addition, known interpolation processing is performed to supplement the read image data. As a result, first volume data is created in which sampling points (referred to as voxels) are arranged at regularly spaced intervals along each of three orthogonal axes. Likewise, the volume data creation section 2 creates second volume data on the basis of image data of the second images and their associated position information.

The volume data storage section 1 stores the first volume data created by the volume data creation section 2 and the volume data storage section 2 stores the second volume data created by the volume data creation section 2.

The plane position setting section 4 is a functional element for setting the position of a desired plane on the volume data interactively and has a graphical user interface (GUI) such as a dialog window display.

The plane coordinate creation section 6 reads the first volume data from the volume data storage section 1 and creates a set of coordinates (depth map) representing that plane section on the first volume data which has been set through the plane position setting section 4 and is orthogonal to the direction of line of sight set by the rendering condition setup section 8.

The rendering condition setup section 8 sets up conditions used for creating a three-dimensional image from the second volume data (in the present embodiment, referred to as a volume rendering image), that is, opacity, color and display direction for each voxel that is a constituent element of the volume data. This display direction is the direction of line of sight orthogonal to a predetermined plane of projection (display surface) as well as is the same as the display direction-of a first three-dimensional image. The opacity and color of the first three-dimensional image (cross-sectional image) are also set up by the rendering condition setup section 8.

The front-region trimming decision section 10 is a functional element for allowing the user to decide whether or not to trim a portion of the second volume data which is situated ahead of the plane set on the first volume data by the plane position setting section 4 and comprises the aforementioned GUI. The term "trimming" used herein does not mean erasing the volume data itself from the volume data storage section 2 but means making no reference to a partial region of the second volume data in the rendering process to be described later, that is, not producing a three-dimensional image based on volume data for that region.

The composite image producing section 12 reads the first and second volume data from the volume data storage sections 1 and 2, respectively, and then performs a rendering process on the first and second volume data along the display direction (i.e., the direction of projection as well as the direction of line of sight) set in the rendering condition setup section 8 to produce a composite (combined) image of the first three-dimensional image (cross-sectional image) based on the first volume data and the second three-dimensional image based on the second volume data. In the rendering process, the rendering conditions, such as opacity, color, etc., set up by the rendering condition setup section 8 are used for each of the first and second three-dimensional images. The rendering is performed taking into consideration whether to trim the front region or not, which has been decided in the front-region trimming decision section 10. The composite image produced by the composite image producing section 12 is sent to the image display unit 14 and then visually displayed.

Hereinafter, a detailed description will be given of the procedure of setting an arbitrary plane on the first volume data, creating a depth map representing the set plane, and producing a composite image of two types of three-dimensional images based on the first and second volume data while referring to the depth map.

Figure 2:
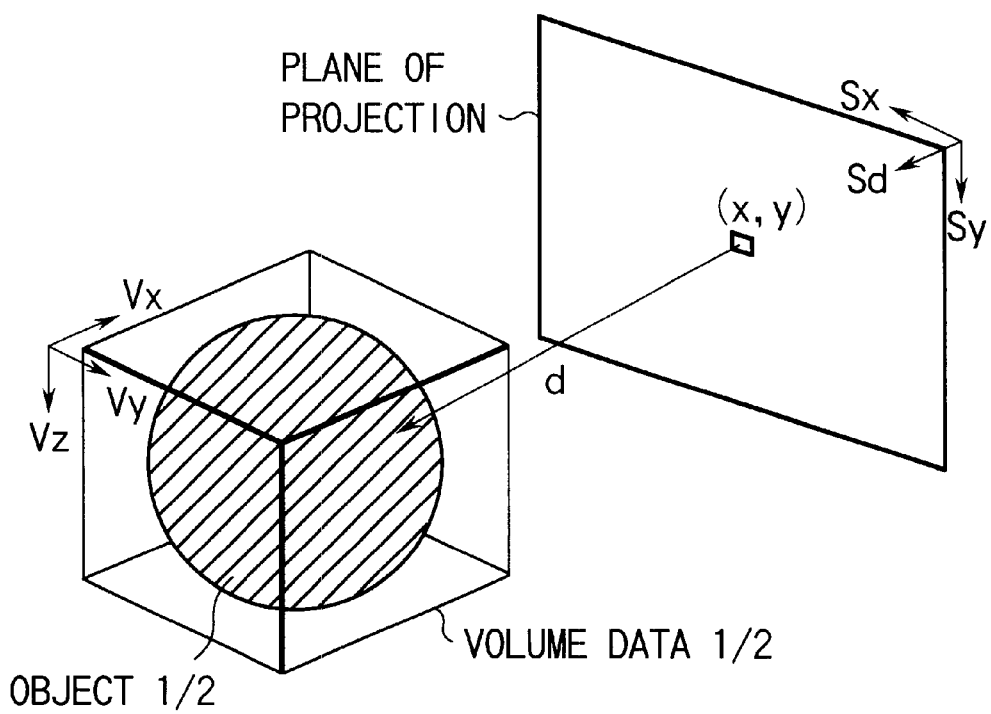
FIG. 2 shows a relationship between first and second volume data and a project plane on which a volume-data-based three-dimensional image is produced.

FIG. 2 shows a relationship between the first and second volume data and a plane of projection on which a three-dimensional image based on both the volume data is produced. As shown, in this embodiment the coordinate system is the same for the first and second volume data. This coordinate system shall be referred to as the volume data coordinate system Vx-Vy-Vz. In FIG. 2, the sphere on the coordinate system Vx-Vy-Vz indicates first and second objects. Here, the first object is a three-dimensional image based on the first volume data, and the second object is a three-dimensional image based on the second volume data. The final image displayed on the display unit 14 consists of projected images of the first and second objects on the plane of projection.

The plane of projection on which the three-dimensional images are projected is defined as a two-dimensional plane perpendicular to the display direction (the direction of line of sight) set up through the rendering condition setup section 8 and its coordinate system shall be referred to as the screen data coordinate system Sx-Sy-Sd. In the screen data coordinate system, the Sd-axis direction is coincident with the direction of line of sight. The length of a line extending along the coordinate axis Sd from the plane of projection to a point on the volume data shall be referred to as depth d.

As described previously, the plane coordinate creation section 6 determines sets of coordinates representing the position of the plane section of the first volume data in accordance with the plane section set by the plane position setting section 4 and the direction of line of sight set by the rendering condition setup section 8.

The plane section on volume data is a region which is displayed as a cross-sectional image (light and shade image) employed for diagnosis by doctors and, at the same time, represents a boundary between the inside and the outside of a region to be displayed as a three-dimensional image, which, for example, allows that portion of a three-dimensional image which is situated this side of the plane section as seen from the viewpoint to be switched between non-display and display. For this reason, thresholds, mathematical expressions and coordinates are set for the plane section as indicated in (1) to (3) below and used as the conditions for determining a displayed region.

(1) When the value of a certain voxel in volume data falls within a set range of thresholds and the value of an adjacent voxel is outside the range, the first-mentioned voxel is set as a voxel on the plane section.

(2) The boundary between the inside and the outside of the range of coordinates represented by the following expression is set as a plane section.

EXAMPLE 1

The coordinates (xs, ys, ds) on the screen data coordinate system that meet the following conditions are included within the displayed region:

$$Lx_s < x_s \&\& x_s < Hx_s \&\& Ly_s < y_s \&\& ys < Hys \&\& Ld_s < ds \&\& d_s < Hd_s$$

EXAMPLE 2

The coordinates (xv, yv, zv) on the volume data coordinate system that meet the following conditions are included within the displayed region:

$$(x_v - Ox_v)^2 + (y_v - Oy_v)^2 + (y_v - Oy_v)^2 < Rv^2$$

(3) Each set of coordinates on the volume data coordinate system or screen data coordinate system is specified to be inside or outside the display region and the resultant boundary is set as the plane section.

In the present embodiment, the position of the plane section in the first volume data is determined as the coordinates on the screen data coordinate system. That is, a two-dimensional arrangement of depths from the screen to the plane section of the displayed region is determined. This arrangement is referred to as a depth map D1(x, y).

Figure 3:
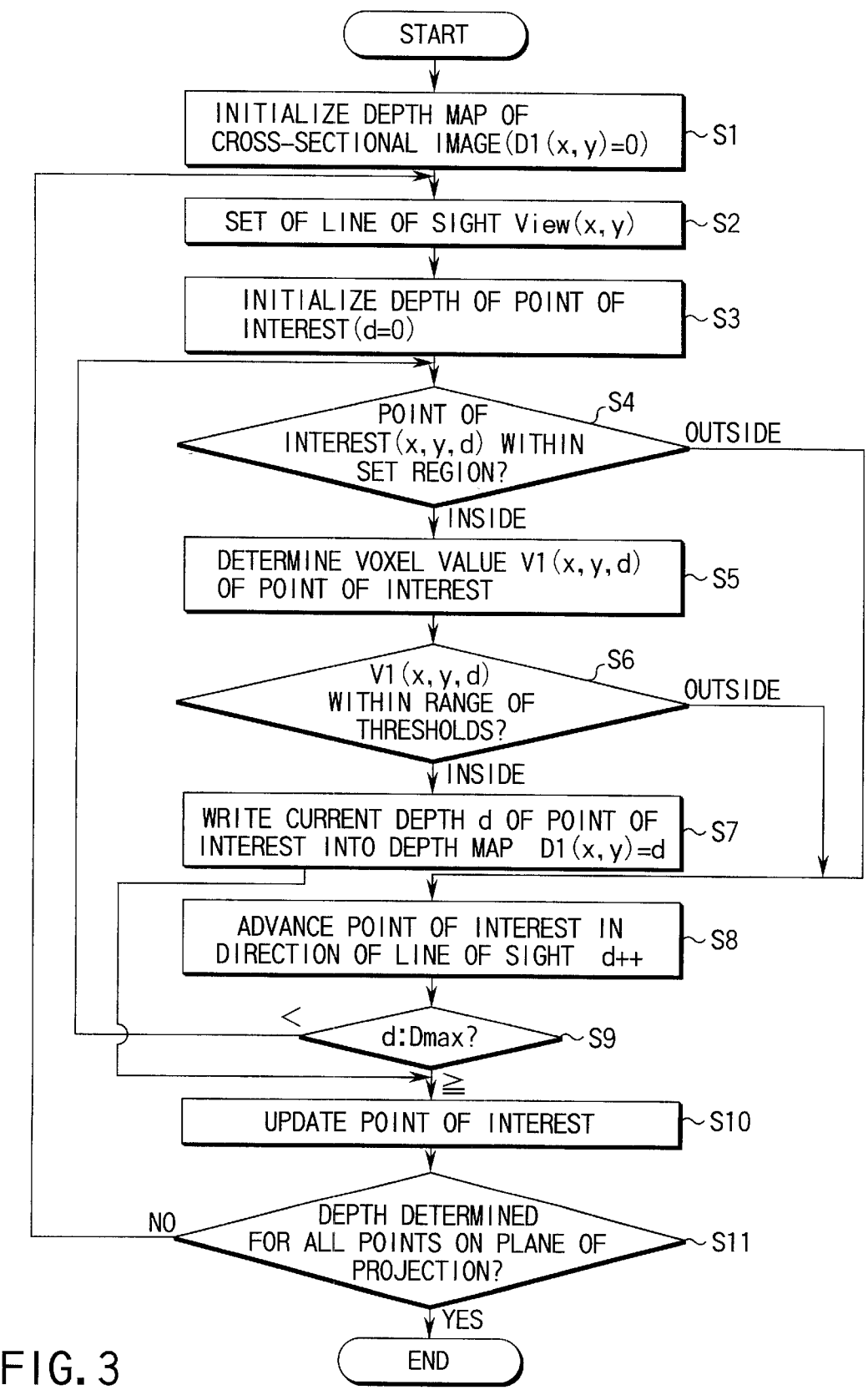
FIG. 3 is a flowchart illustrating the procedure of producing a depth map.

FIG. 3 is a flowchart for the procedure of creating the depth map.

First, in step S1, the depth map, D1(x, y), of the cross-sectional image is initialized to all zeros (0, 0). Then, the direction of line of sight, View (x, y), that passes through coordinates (x, y) on the plane of projection in the screen coordinate system is initialized. Next, the depth, d, of a point of interest is initialized to, say, 0, in which case that point is present on the plane of projection.

Next, the depth, d, of a point (x, y) on the depth map is determined as follows:

First, a decision is made as to whether the point (x, y, d) of interest is included outside or inside a set region in object 1 (step S4).

If, in step S4, the decision is that the point of interest is outside the set region, then the depth of the point of interest is increased by the amount corresponding to the size of one voxel along the direction of line of sight (step S8) and the procedure then returns to step S4. If, on the other hand, the point of interest is included inside the set region, then the voxel values V1(x, y, d) of the point of interest are determined (step S5) and a decision is then made as to whether or not the point of interest is within the set threshold range (step S6). Such threshold processing permits objects to be displayed to be extracted from the first volume data.

If, in step S6, the decision is that the voxel value of the point of interest is outside the set threshold range, then the procedure goes to step S8 to increase the depth of the point of interest along the direction of line of sight. If, on the other hand, the voxel value of the point of interest is included inside the set range of thresholds, then the depth, d, of the point of interest is written into the depth map D1(x, y) (step S7), terminating the calculation of the depth, d, of the point of interest on the plane of projection.

When the depth of the point of interest has reached the maximum depth, the depth of the point of interest is set as Dmax, terminating the calculation of the depth of this point (x, y)(step S9).

The coordinates (x, y) of the interest of point on the plane of projection are updated to provide a new point of interest (step S10). Steps S2 through S11 are repeated until the depths of all the points (pixels) on the plane of projection are determined. As a result, the depth map D1(x, y) is created.

As described previously, the final image displayed on the display unit 14 is projected images of the first and second objects on the plane of projection. Since the volume data coordinate system Vx-Vy-Vz is the same for the first and second volume data and the first and second objects are projected onto the same plane of projection, the final image is a composite of projected images of the first and second objects.

Figure 4:
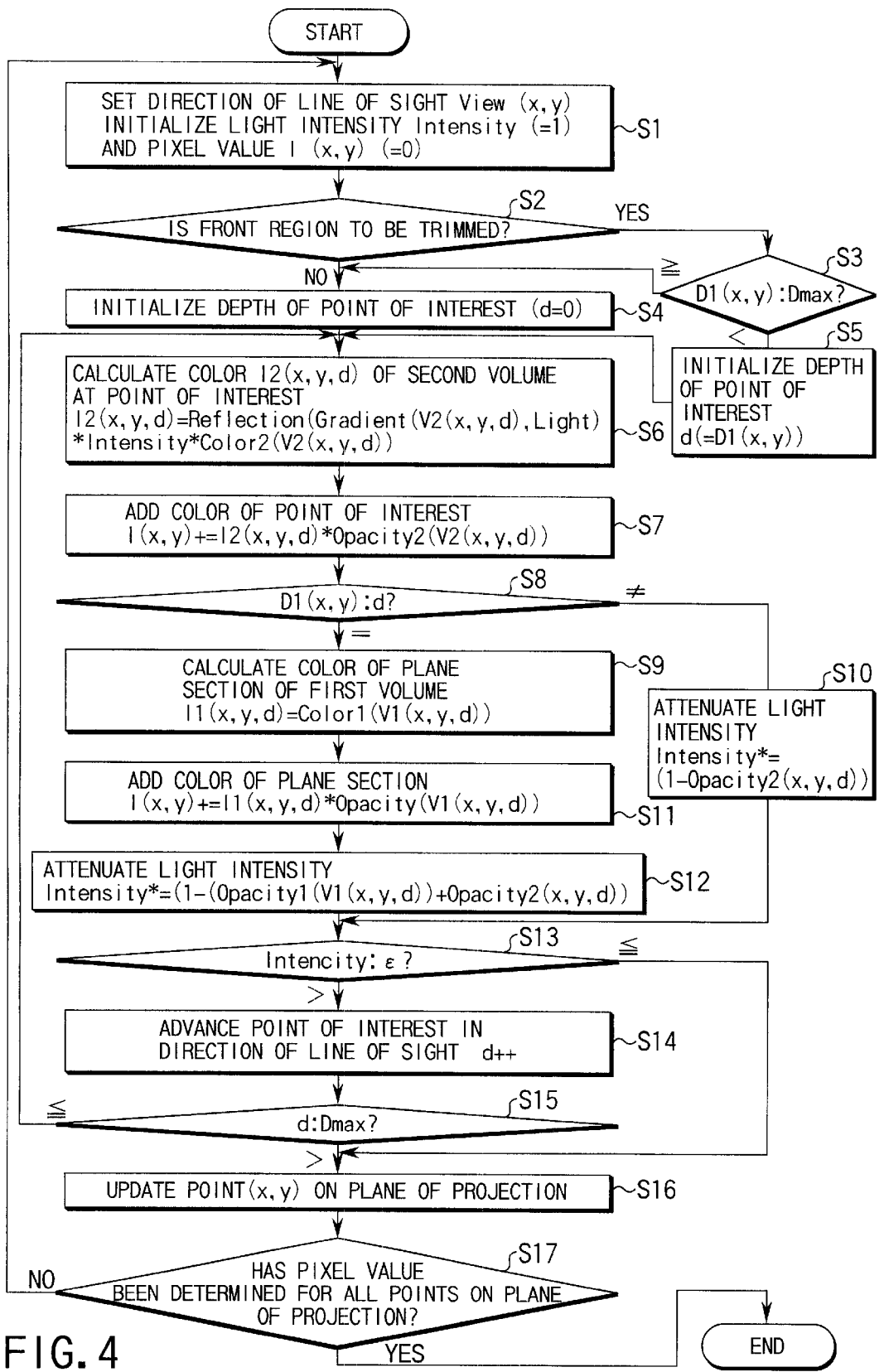
FIG. 4 is a flowchart illustrating the procedure of producing a three-dimensional composite image.

FIG. 4 is a flowchart for the procedure of producing the composite image.

First, in step S1, in determining the pixel value i(x, y) at a point of interest on the plane of projection, the direction of line of sight, View(x, y), passing through that point is set and the intensity of light passing through that point is initialized to 1. Further, the pixel value i(x, y) is initialized to 0.

Next, in step S2, a decision is made as to whether the front region has been specified to be trimmed or not in the front-region trimming decision section 10. If NO, the initial position of the point of interest is set on the plane of projection. That is, the depth, d, of the point of interest is initialized to 0 (step S4).

If, on the other hand, the front region has been specified to be trimmed, then the depth map is examined for the value D1(x, y) at the point (x, y) of interest to decide whether the value is less than the maximum depth Dmax (step S3). If less than Dmax, the initial position of the point of interest is set on the plane section. That is, the depth d is set to D1(x, y) (step S5). If D1(x, y) is equal to or more than Dmax, then the initial position of the point of interest is set on the plane of projection. That is, the depth d is initialized to 0 (step S4). Thus, whether to set the initial position of the point of interest on the plane of projection or on the plane section indicated by the depth map depends on whether or not the front region has been set to be trimmed, which allows a region for which a three-dimensional image (i.e., an imaging region) is produced to be changed with reference to the volume data.

Next, the color, i2(x, y, d), of the point of interest in the second volume data is calculated from the density gradient vector Gradient(V2(x, y, d)), the light direction vector Light and the light intensity Intensity of the second volume data in the neighborhood of the point of interest and the color Color2(V2(x, y, d)) set on the basis of the voxel value V2(X, y, d) of the second volume data at the point of interest (step S6).

The calculation in this case may be made using the following expression that is generally used in the volume rendering:

$$I2(x,y,d)=\text{Reflection}(\text{Gradient}(V2(x,y,d)), \text{Light}*\text{Intensity}*\text{Color2}(V2(x,y,d)) \quad (1)$$

For the details of the volume rendering, see R. A. Drebin et al., "Volume Rendering", Computer Graphics 22(4), 1988, 65–74.

The value obtained by multiplying the color, i2(x, y,d), of the point of interest in the second volume data determined from the above expression by the opacity, Opacity2(V2(x, y,d)), of the second volume data is added to the pixel value i(x,y) (step S7). The expression therefor is given by $$1(x,y)+=I2(x,y,d)*\text{Opacity2}(V2(x,y,d)) \quad (2)$$

Note here that A+=B is equivalent to A=A+B.

A decision is then made as to whether or not the depth, d, of the point of interest corresponds to the position of the plane section of the first volume (step S8). The position of the plane section of the first volume can be known from the depth map D1(x,y) already formed.

When the depth of the point of interest corresponds to the position of the plane section of the first volume, the color, Color(V1(x,y,d)), based on the voxel value, V1(x,y,d), of the first volume data, i.e., the color of the plane section I1(x,y,d) is first calculated in step S9 by $$I1(x,y,d)=\text{Color1}(V1(x,y,d)) \quad (3)$$

Next, the color, I1(x,y,d), is multiplied by opacity, Opacity1(V1(x,y,d)), and then added to the pixel value I(x,y). Namely, the color of the plane section is added to the pixel value (step S11). This calculation is made by $$I(x,y)+=I1(x,y,d)*\text{Opacity1}V1(x,y,d)) \quad (4)$$

Further, the light intensity, Intensity, is decreased according the opacity, Opacity1(V1(x,y,d)), of the first volume data and the opacity, Opacity2(V2(x,y,d)), of the second volume data as follows:

$$\text{Intensity}*=(1-(\text{Opacity1}(V1(x,y,d)))+\text{Opacity2}(V2(x,y,d))) \quad (5)$$

Note here that A*=B is equivalent to A=A*B.

If, on the other hand, the decision in step S8 is that the depth, d, of the point of interest does not correspond to the position of the plane section of the first volume, then the light intensity, Intensity, is decreased based on only the opacity, Opacity2(V2(x,y,d)), of the second volume data independently of the color of the plane section (step S10). This calculation is made by $$\text{Intensity}^* = (1 - (\text{Opacity2}(V2(x,y,d))) \tag{6}$$

A decision is then made as to whether the light intensity is greater than the minimum intensity $\epsilon$(step S13).

If the light intensity is greater than the minimum intensity $\epsilon$, then the point of interest is advanced by the distance corresponding to the size of one voxel in the direction of line of sight (step S14). If, at this point, the light intensity is greater than the minimum intensity $\epsilon$ and the depth, d, of the point of interest, is not greater than the maximum depth Dmax, then the calculation of the pixel value I(x,y) for the advance point of interest is repeated beginning with step S6.

If, on the other hand, the light intensity is not greater than the minimum intensity $\epsilon$ or the depth, d, of the point of interest is greater than the maximum depth Dmax, then the calculation of pixel value for the point of interest (x,y) is terminated, the coordinates (x,y) of the point of interest on the plane of projection are updated, and the calculation of the pixel value for the next point of interest is commenced (step S17). The above processes are repeated for all the pixels on the plane of projection.

Figure 5:
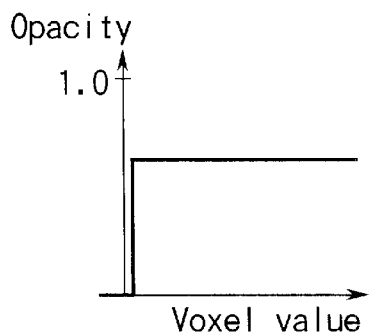
FIG. 5 shows opacity versus voxel value for the first volume data.

FIG. 5 shows an example of opacity set for the first volume data. If the opacity is set to unity, then the region behind the plane section will become invisible. On the other hand, if the opacity is set to less than unity, the region behind the plane section will become visible depending on the opacity.

Figure 6:
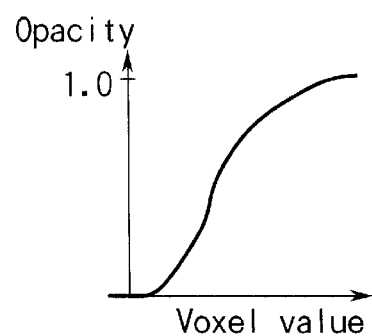
FIG. 6 shows opacity versus voxel value for the second volume data.

FIG. 6 shows an example of opacity set for the second volume data. When the second volume data represents blood flow rates as in this embodiment, a volume rendering image in which regions having much blood flow are imaged vividly can be obtained by setting high opacity to voxels having much blood flow and low opacity to voxels having little blood flow.

Figure 7:
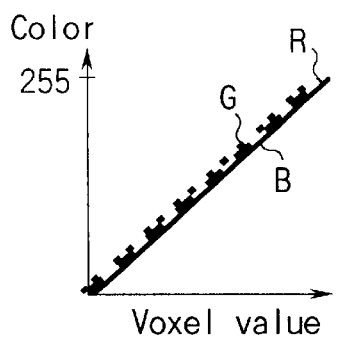
FIG. 7 shows color versus voxel value for the first volume data.
Figure 8:
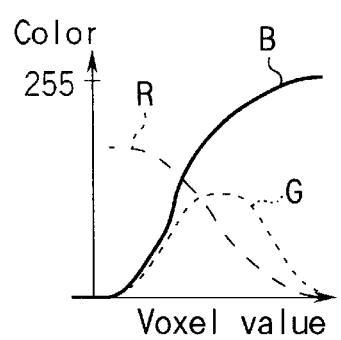
FIG. 8 shows color versus voxel value for the second volume data.

FIGS. 7 and 8 show exemplary color conditions which are set up on the first and second volume data, respectively. If the same value is assigned to the red, green and blue components for each voxel (value) as shown in FIG. 7 (three straight lines representing color conditions for red, green and blue components become aligned with one another), then the cross-sectional image represented by the first volume data becomes a black and white image. On the other hand, if a different value is assigned to each of the red, green and blue components for each voxel (value) as shown in FIG. 8, then the three-dimensional image represented by the second volume data becomes a color image.

Figure 9A:
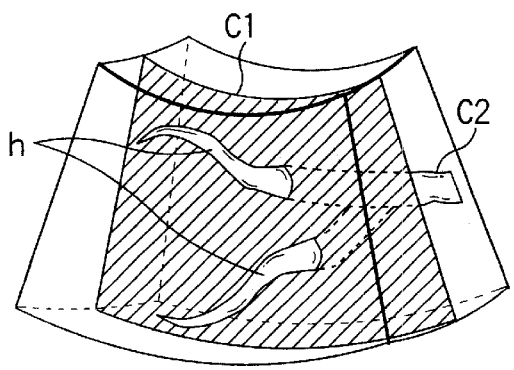
FIG. 9A shows a first composite image displayed on the display unit.
Figure 9B:
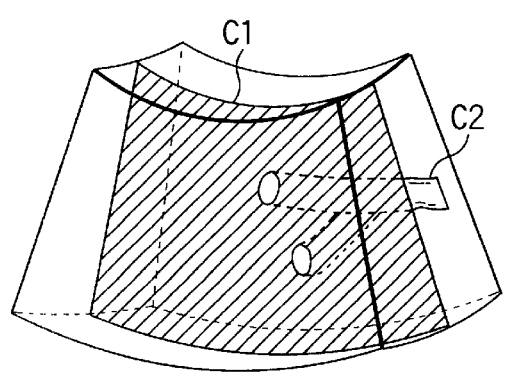
FIG. 9B shows a second composite image displayed on the display unit.

FIGS. 9A and 9B show examples of composite images produced by the above processing and displayed on the display unit 14.

C1 indicates a three-dimensional image (B-mode cross-sectional image) based on the first volume data. A plane passing through the center of the volume is specified to be the plane section. C2 indicates a three-dimensional image (blood-flow Doppler image) based on the second volume data. The positions on the plane section that represent blood flow regions and the rendering conditions therefor are set on the image C2. n indicates portions situated this side of the plane section (C1) in the direction of line of sight.

When the front-region trimming decision section 10 is instructed by the observer to trim the front region, the portions n situated ahead of the cross-sectional image are cut away and the cuts of the blood flow regions are displayed on the cross-sectional image as shown in FIG. 9B.

The entire composite image can be rotated by reperforming rendering under changed rendering conditions. Namely, the direction of display (direction of line of sight) can be varied. In addition, the position and shape of the plane section can be changed. Moreover, by changing weights of opacity on the section of the blood flow Doppler image when the section 10 is set to cut away the front region, the form of display can be changed appropriately.

According to the embodiment described above, in the processing of a point of interest along the direction of line of sight, by setting the initial position of the point of interest either on the plane section indicated by the depth map or on the plane of projection according to whether the trimming of the front region has been specified, a region for which a three-dimensional image (i.e., an imaging region) is produced can be changed with reference to the volume data. This allows display control such that those portions of blood vessels which run ahead of the plane section in the direction of viewpoint are not imaged temporarily (the image of blood vessels ahead of the plane section are temporarily placed in the non-displayed state) and a cross-sectional image of the blood vessels are displayed superimposed on a sectional image of a tumor. Such display control allows a relationship between the running state of the blood vessels and the internal structure of the tumor to be recognized correctly and readily.

According to the present embodiment, therefore, a three-dimensional medical image composite display device can be provided which produces an image useful in imaging diagnosis and treatment by performing three-dimensional image composition processing on first and second volume data respectively obtained for the same region of a human body under examination by the B- and Doppler-mode imaging techniques.

The other embodiments of the medical image processing device of the present invention will be described next.

The above embodiment has been described in terms of a three-dimensional medical image composite display device in which the medical image processing device of the present invention is combined with an ultrasonic imaging diagnostic apparatus. In this embodiment, the medical image processing device of the present invention is combined with various imaging diagnostic apparatuses other than ultrasonic diagnostic apparatus, such as a X-ray computerized tomography (CT) apparatus, a magnetic resonance imaging (MRI) apparatus, a nuclear medical diagnostic apparatus, etc.

First, the ultrasonic diagnostic apparatus is characterized in that a B-mode image which is a tissue image and a color Doppler or power Doppler image which is a blood flow image can be collected simultaneously through the same scanning of ultrasound. By producing a first three-dimensional image using B-mode images and producing a second three-dimensional image using color Doppler or power Doppler images and then displaying both the images in combination, a three-dimensional position relationship between tissues and moving objects (e.g., blood flow) can be identified effectively.

With the magnetic resonance imaging (MRI) apparatus, various imaging techniques have been developed. A water or fat distribution image or a blood flow image can be obtained by making a selection among the imaging techniques.

Unlike the ultrasonic diagnostic apparatus, the MRI apparatus is not capable of simultaneously obtaining different types of images for the same region of a human body under examination. Thus, different types of imaging are carried out in succession with the human body laid down, whereby different types of images for the same region can be obtained in succession. For example, a morbid portion weighted image is first collected as a first three-dimensional image and then a blood flow image is collected as a second three-dimensional image. Both the images are combined in accordance with the principles of the invention and then displayed. This allows a three-dimensional position relationship between the morbid portion and the blood flow to be displayed effectively.

In addition, images captured by different imaging diagnostic apparatuses (modalities) may be displayed in combination. For example, the X-ray computerized tomography (CT) apparatus is capable of producing images which, while being inferior in contrast to MRI images, are vivid in soft tissues or bone tissues. Moreover, blood flow or morbid portion weighted images can be obtained by injecting contrast medium into a human body under examination.

An image collected by the MRI apparatus and an image collected by the X-ray CT apparatus are combined. However, in some cases both the images cannot be simply combined for subsequent comparative observation because they were collected by different modalities and are therefore not coincident with each other in position and magnification.

To overcome such a drawback, a medical image processing device described in Japanese Unexamined Patent Publication No. 10-137190 assigned to the same assignee as the present application may be employed. That is, volume data are prepared from images collected by different modalities so that the images may be combined with each other by bringing them in registration with each other so as to allow comparative observation. Thereafter, the resultant images are subjected to the inventive three-dimensional image composition processing described so far.

The nuclear medical diagnostic apparatus, such as an SPEC apparatus, can image functional information of a human body under examination by properly selecting nuclear species and medicines used.

As in the case of X-ray CT apparatus and MRI apparatus, comparative observation may not be made simply by combining images for the same region of a human body under examination collected by SPECT apparatus and X-ray CT apparatus. For this reason, the arrangement of the image processing device described in the above application is used to make the X-ray CT image and the SPECT image coincident with each other in their three-dimensional position relationship. The medical image processing device described in the above application is arranged to select multiple images on the basis of anatomical morphological information, then determine the relative position relationship between the selected images and bring the selected images in registration with each other.

By producing a composite image of a first three-dimensional image produced from images of bones and soft tissues obtained by the X-ray CT apparatus and a second three-dimensional image produced from functional images obtained by the SPECT apparatus, an effective display in which the morphology and the function of an object are associated with each other can be made.

Although the preferred embodiments of the present invention have been disclosed and described, it is apparent that other embodiments and modifications are possible. For example, although the embodiments have been described in terms of composite display of two types of three-dimensional (volume) data, the principles of the invention is applicable to composite display of three or more types of three-dimensional data.

According to the present embodiment, as described above, a three-dimensional medical image composite display device can be provided which produces an image useful in imaging diagnosis and treatment by performing three-dimensional image composition processing on two or more types of volume data obtained for the same region of a human body under examination by different imaging techniques (while changing imaging regions in the volume data).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image processing device for producing multiple three-dimensional images for the same region of a human body under examination as seen from a direction of line of sight and producing a composite image of the three-dimensional images, comprising:

means for setting a plane section of the region of the human body under examination;

first producing means responsive to the input of first volume data on the region of the human body under examination for producing a first three-dimensional image containing the plane section set by the setting means on the basis of the first volume data, said first producing means including depth map producing means for producing a depth map representing the plane section on the first volume data;

second producing means responsive to the input of second volume data on the region of the human body under examination for producing a second three-dimensional image on the basis of the second volume data, wherein said second producing means trims a portion of the second volume data corresponding to space situated ahead of the plane section as seen from the direction of line of sight; and composition means for producing a composite image of the first three-dimensional image produced by the first producing means and the second three-dimensional image produced by the second producing means while referring to sad depth map.

2. The medical image processing device according to claim 1, further comprising display means for selectively displaying the second three-dimensional image and another second three-dimensional image produced on the basis of the whole of the second volume data.

3. The medical image processing device according to claim 1, wherein the composition means produces a composite image of the first three-dimensional image based on the first volume data and a three-dimensional image containing the plane section and based on the second volume data.

4. The medical image processing device according to claim 3, further comprising means for changing the transparency of the three-dimensional image based on the second volume data.

5. The medical image processing device according to claim 1, wherein at least one of the position and shape of the plane section set by the setting means is set variable.

6. A medical image processing device for producing a plurality of three-dimensional images for the same region of a human body under examination as seen from a direction of line of sight and combining the three-dimensional images to produce a composite image for display, comprising:

input means for setting a plane section of the region of the human body under examination;

first image projection means, responsive to first three-dimensional data for the same region of the human body under examination, for producing a three-dimensional image containing the plane section set by the input means, said first image projection means including depth map producing means for producing a depth map representing the plane section on the first three-dimensional data;

input means for specifying the display/non-display of a region of the human body under examination;

second image producing means, responsive to second three-dimensional image data for the same portion of the human body under examination, for producing a three-dimensional image based on said second three-dimensional image data, wherein said second image producing means trims data on one side of the plane; and combining means for combining the three-dimensional image containing the plane section produced by the first image producing means and the three-dimensional image produced by the second image production means while referring to said depth map.

7. The medical image processing device according to claim 6, wherein the first three-dimensional data is three dimensional ultrasonic imaging data representing the configuration of tissues and the second three-dimensional data is three dimensional ultrasonic imaging data representing blood flow information.

8. The medical image processing device according to claim 6, wherein the medical image processing device is an ultrasonic diagnostic apparatus.

9. An image display method for use with a medical image processing device for producing a plurality of three-dimensional image for the same region of a human body under examination and combining the three-dimensional image to produce a composite image for display, the method comprising the steps of:

the step of setting a plane section of the region of the human body under examination;

the step of creating a depth map representing said plane section;

the step of, when the display of data is specified through input means, combining a first three-dimensional image and a second three-dimensional image, each containing the plane section of the region set by the setting step to produce a composite image for display, wherein said step of combining is performed while referring to said depth map; and the steps of, when the non-display of data is specified through input means, trimming the second three-dimensional image having data on one side of the plane section, and combining the first three-dimensional image containing the plane section of the region and the trimmed second three-dimensional image to produce a composite image for display.

* * * * *